United States Patent
Kubalak et al.

[11] Patent Number: 6,039,750
[45] Date of Patent: Mar. 21, 2000

[54] URETHRAL OCCLUSION DEVICE FOR MAINTAINING URINARY BLADDER RETENTION AND METHOD OF USE

[75] Inventors: Thomas P. Kubalak, Plymouth, Minn.; Peter Sheperd, Santa Barbara, Calif.; Jeffrey P. LaPlante, Minneapolis, Minn.

[73] Assignee: Mentor Corporation, Santa Barbara, Calif.

[21] Appl. No.: 08/838,724

[22] Filed: Apr. 10, 1997

Related U.S. Application Data

[63] Continuation-in-part of application No. 08/760,906, Dec. 3, 1996.

[51] Int. Cl.[7] .................................................. A61B 17/00
[52] U.S. Cl. .................................. 606/201; 128/DIG. 25; 604/352; 600/41
[58] Field of Search .............................. 606/201; 602/61; 128/885, DIG. 25; 600/41; 604/352

[56] References Cited

U.S. PATENT DOCUMENTS

| | | | |
|---|---|---|---|
| Re. 33,206 | 5/1990 | Conway et al. ........................ | 604/349 |
| 678,943 | 7/1901 | Davis . | |
| 1,133,958 | 3/1915 | Henderson . | |
| 1,728,322 | 9/1929 | Badrian . | |
| 1,748,227 | 2/1930 | Hyams . | |
| 1,750,654 | 3/1930 | Wappler . | |
| 2,371,883 | 3/1945 | Gammeter et al. ........................ | 18/58 |
| 2,389,831 | 11/1945 | Welsh ........................................ | 2/21 |
| 2,455,859 | 12/1948 | Foley ..................................... | 128/346 |
| 2,533,924 | 12/1950 | Foley ..................................... | 128/346 |
| 2,618,270 | 11/1952 | Pearson, Jr. ........................... | 128/346 |
| 2,756,753 | 7/1956 | Means .................................... | 128/346 |
| 3,147,754 | 9/1964 | Koessler ................................ | 128/346 |
| 3,155,096 | 11/1964 | Outwin .................................. | 128/346 |
| 3,203,421 | 8/1965 | Bialick .................................. | 128/346 |
| 3,520,305 | 7/1970 | Davis ..................................... | 128/295 |
| 3,608,552 | 9/1971 | Broerman ............................... | 128/295 |
| 3,636,984 | 1/1972 | Rauhauser ............................. | 138/155 |

(List continued on next page.)

FOREIGN PATENT DOCUMENTS

| | | |
|---|---|---|
| 0 506 300 A2 | 9/1992 | European Pat. Off. . |
| 27 17 924 A1 | 10/1978 | Germany . |

*Primary Examiner*—Corrine McDermott
*Assistant Examiner*—N. Kent Gring
*Attorney, Agent, or Firm*—Fish & Richardson P.C., P.A.

[57] ABSTRACT

A urethral occlusion device having a very malleable, flexible, deformable polymer occlusion band which may be easily wrapped about the exterior of the penis to provide sufficient pressure to prevent urine flow, but without restricting blood circulation. The occlusion band includes a silicone rubber shell with silicone gel liner surfaces which provide a washable, reusable, skin-sensitive bond when wrapped, and allow the band to be tightened to the patient's desired degree of compression. A plurality of pliant, deformable ribs are positioned on the occlusion band and oriented along the underside of the penis to mildly stretch the urethra to an occluded position. An elastomeric cincture ring may also be added circumscribing the occlusion band to apply additional compressive pressure, the cross-sectional area of each of the three finger-engaging rings being greater than that of the central pressure-exerting ring so that an outward stretching force will deform the central pressure-exerting ring more than the finger-engaging rings.

45 Claims, 4 Drawing Sheets

U.S. PATENT DOCUMENTS

| | | | |
|---|---|---|---|
| 3,645,835 | 2/1972 | Hodgson | 161/146 |
| 3,683,901 | 8/1972 | Wegener | 128/79 |
| 3,739,783 | 6/1973 | Broerman | 128/295 |
| 3,788,324 | 1/1974 | Lim | 128/295 |
| 3,789,828 | 2/1974 | Schulte | 128/1 R |
| 3,835,857 | 9/1974 | Rogers, III et al. | 128/295 |
| 3,863,638 | 2/1975 | Rogers, III et al. | 128/295 |
| 3,866,611 | 2/1975 | Baumrucker | 128/346 |
| 3,898,993 | 8/1975 | Taniguchi | 128/349 |
| 4,187,851 | 2/1980 | Hauser | 128/295 |
| 4,202,335 | 5/1980 | Gold | 128/295 |
| 4,367,732 | 1/1983 | Poulsen et al. | 128/156 |
| 4,378,018 | 3/1983 | Alexander et al. | 128/295 |
| 4,475,910 | 10/1984 | Conway et al. | 604/352 |
| 4,477,325 | 10/1984 | Osburn | 204/159 |
| 4,534,353 | 8/1985 | de Leur et al. | 128/346 |
| 4,539,980 | 9/1985 | Chaney | 128/79 |
| 4,581,026 | 4/1986 | Schneider | 604/352 |
| 4,626,250 | 12/1986 | Schneider | 604/352 |
| 4,628,915 | 12/1986 | Chaney | 128/79 |
| 4,638,790 | 1/1987 | Conway et al. | 128/138 R |
| 4,640,688 | 2/1987 | Hauser | 604/352 |
| 4,710,169 | 12/1987 | Christopher | 604/104 |
| 4,713,067 | 12/1987 | Rothenberg et al. | 604/353 |
| 4,731,064 | 3/1988 | Hayden | 604/352 |
| 4,759,753 | 7/1988 | Schneider et al. | 604/352 |
| 4,800,900 | 1/1989 | French | 128/885 |
| 4,820,289 | 4/1989 | Coury et al. | 604/349 |
| 4,820,291 | 4/1989 | Terauchi et al. | 604/349 |
| 4,846,909 | 7/1989 | Klug et al. | 156/232 |
| 4,855,169 | 8/1989 | McGlothlin et al. | 428/35.2 |
| 4,856,498 | 8/1989 | Osbon | 128/79 |
| 4,885,049 | 12/1989 | Johannesson | 156/289 |
| 4,957,487 | 9/1990 | Gerow | 604/133 |
| 4,963,137 | 10/1990 | Hayden | 604/349 |
| 4,991,574 | 2/1991 | Pocknell | 128/156 |
| 5,017,625 | 5/1991 | Ansell | 521/159 |
| 5,045,075 | 9/1991 | Ersek | 604/317 |
| 5,051,259 | 9/1991 | Olsen et al. | 424/443 |
| 5,067,965 | 11/1991 | Ersek et al. | 623/66 |
| 5,078,707 | 1/1992 | Klug | 604/349 |
| 5,087,248 | 2/1992 | Beisang, III | 604/180 |
| 5,102,405 | 4/1992 | Conway et al. | 604/352 |
| 5,112,957 | 5/1992 | Pollard | 530/387.1 |
| 5,128,088 | 7/1992 | Shimomura et al. | 264/305 |
| 5,156,601 | 10/1992 | Lorenz et al. | 604/307 |
| 5,176,666 | 1/1993 | Conway et al. | 604/349 |
| 5,184,629 | 2/1993 | Erickson et al. | 128/885 |
| 5,234,402 | 8/1993 | Osbon | 600/41 |
| 5,267,989 | 12/1993 | Moyet-Ortiz | 604/349 |
| 5,306,227 | 4/1994 | Osbon et al. | 600/41 |
| 5,306,504 | 4/1994 | Lorenz | 424/449 |
| 5,312,383 | 5/1994 | Kubalak | 604/350 |
| 5,331,027 | 7/1994 | Whitbourne | 524/37 |
| 5,334,175 | 8/1994 | Conway et al. | 604/352 |
| 5,376,085 | 12/1994 | Conway et al. | 604/352 |
| 5,380,311 | 1/1995 | Bailly | 604/349 |
| 5,380,312 | 1/1995 | Goulter | 604/352 |
| 5,395,344 | 3/1995 | Beisang, III et al. | 604/180 |
| 5,513,654 | 5/1996 | Delson | 128/844 |
| 5,554,141 | 9/1996 | Wendler | 604/352 |
| 5,579,784 | 12/1996 | Harari | 128/844 |
| 5,618,302 | 4/1997 | Martin | 606/201 |

URETHRAL OCCLUSION DEVICE FOR MAINTAINING URINARY BLADDER RETENTION AND METHOD OF USE

RELATED APPLICATIONS

This is a continuation-in-part (CIP) of U.S. patent application Ser. No. 08/760,906 filed on Dec. 3, 1996, pending and the benefit of priority pursuant to 35 USC §120 is hereby claimed from that application. Its specification is fully incorporated herein by reference.

BACKGROUND OF THE INVENTION

1. Field of the Invention

The present invention relates to devices for retaining urine within the bladder of a male patient by accomplishing urethral occlusion from the exterior of the penis.

2. Brief Description of the Prior Art

Various devices for treating urinary incontinence in males are know to the art which utilize a clamping or compressive force on the exterior of the penis to close the urethra. These devices generally rely on a mechanical or pneumatic source of pressure along the underside of the penis, and focus that pressure along a ridge or band extending parallel with the urethra. These devices tend to apply sufficient pressure to pinch or close the urethra, thereby retaining urine within the bladder of the patient until the device is selectively removed for voiding.

Many of these devices present a fairly large profile for the patient to wear comfortably and unnoticeably, as well as a bulky mechanism or complex array of components and connections that may be difficult to operate and inconvenient in other aspects of daily usage. In addition, many of these devices have limited effectiveness, if any. While some may provide sufficient pressure to accomplish urethral closure, they may also tend to restrict or interrupt blood flow via the arteries of the corpus cavernosa and branches of the dorsal artery of the penis, thereby presenting the risk for injury or damage to the vascular system of the penis and mitigating against extended usage of the devices. Several representative examples of these devices are shown and described in detail in the various patents submitted with this disclosure and made of record in the file history hereof to show the general state of art in this field.

Also known to the art are several types of high-compression elastomeric rings for treating impotence by encircling the penis and occluding blood flow from the corpus cavernosa, these rings sometimes being used in combination with a vacuum chamber to enhance the patient's erection prior to the ring being applied. Some variations of these compression rings are designed to permit urethral flow for ejaculate. While such devices effectively accomplish a result which is diametrically opposite to that of a urethral occlusion device for treating urinary incontinence, several representative examples are shown and described in detail in the various patents submitted with this disclosure and made of record in the file history hereof for the purpose of showing the general state of that field of art.

SUMMARY OF THE INVENTION

Briefly described, the urethral occlusion device of this invention provides a very malleable, flexible, deformable polymer occlusion band which may be easily wrapped about the exterior of the penis to provide sufficient pressure to prevent urine flow, but without restricting blood circulation. The occlusion band includes a silicone rubber shell with silicone gel liner surfaces which provide a washable, reusable, skin-sensitive bond when wrapped, and allow the band to be tightened to the patient's desired degree of compression. A plurality of deformable ribs are positioned on the occlusion band and oriented along the underside of the penis to mildly stretch the urethra to an occluded position. Three ribs of varying height have proven suitable. A deformable elastomeric cincture ring may also be added circumscribing the occlusion band to apply additional compressive pressure and further maintain the device in place. In the cincture band, the cross-sectional area of the three equidistant finger-engaging rings are greater than the corresponding cross-sectional area of the central pressure-exerting ring, so that outward stretching force deforms the central pressure-exerting ring more than the finger-engaging rings are deformed.

The urethral occlusion device of this invention may be worn comfortably and virtually unnoticeably by a patient for extended periods of time, and selectively and temporarily removed for voiding and subsequently reapplied for continued reuse. The device may be washed without adversely affecting the quality of the adhesive bond provided by the silicone gel liner. The device has a very small profile, is light weight, and will not irritate or damage the patient's skin when used for extended periods. The device is substantially translucent, thereby minimizing its visual appearance, and will conform to the patient's anatomy to prevent discomfort and injury, or restrict movement when the patient sits, crosses his legs, or engages in strenuous or athletic activity.

BRIEF DESCRIPTION OF THE DRAWINGS

FIG. 12 is a cross section view of a portion of the cincture band of FIG. 11 taken through line 12—12 in FIG. 11a.

DETAILED DESCRIPTION OF THE PREFERRED EMBODIMENTS

The urethral occlusion device of this invention and its method of use are illustrated in FIGS. 1–12, and the invention is referenced generally therein by the numeral 10. The urethral occlusion device, its method of use, components, and techniques described herein for its fabrication are generally referred to interchangeably in this specification as the urethral occlusion device 10 for convenience.

Figure 1:
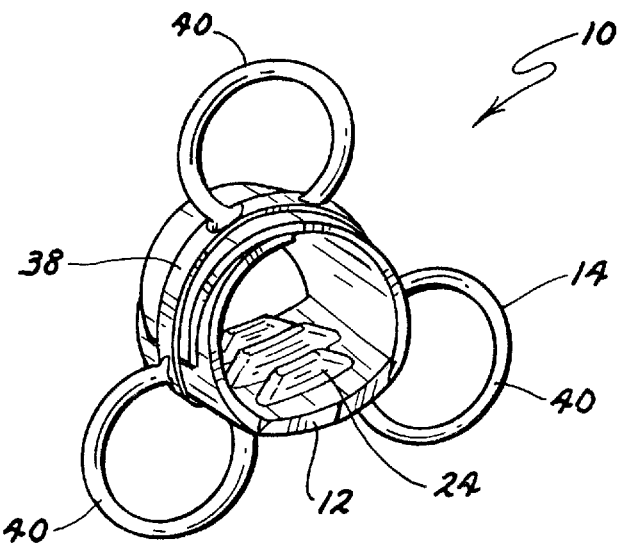
FIG. 1 is a perspective view of one embodiment of the urethral occlusion device of this invention showing the occlusion band in a wrapped configuration with the cincture band surrounding it.
Figure 2:
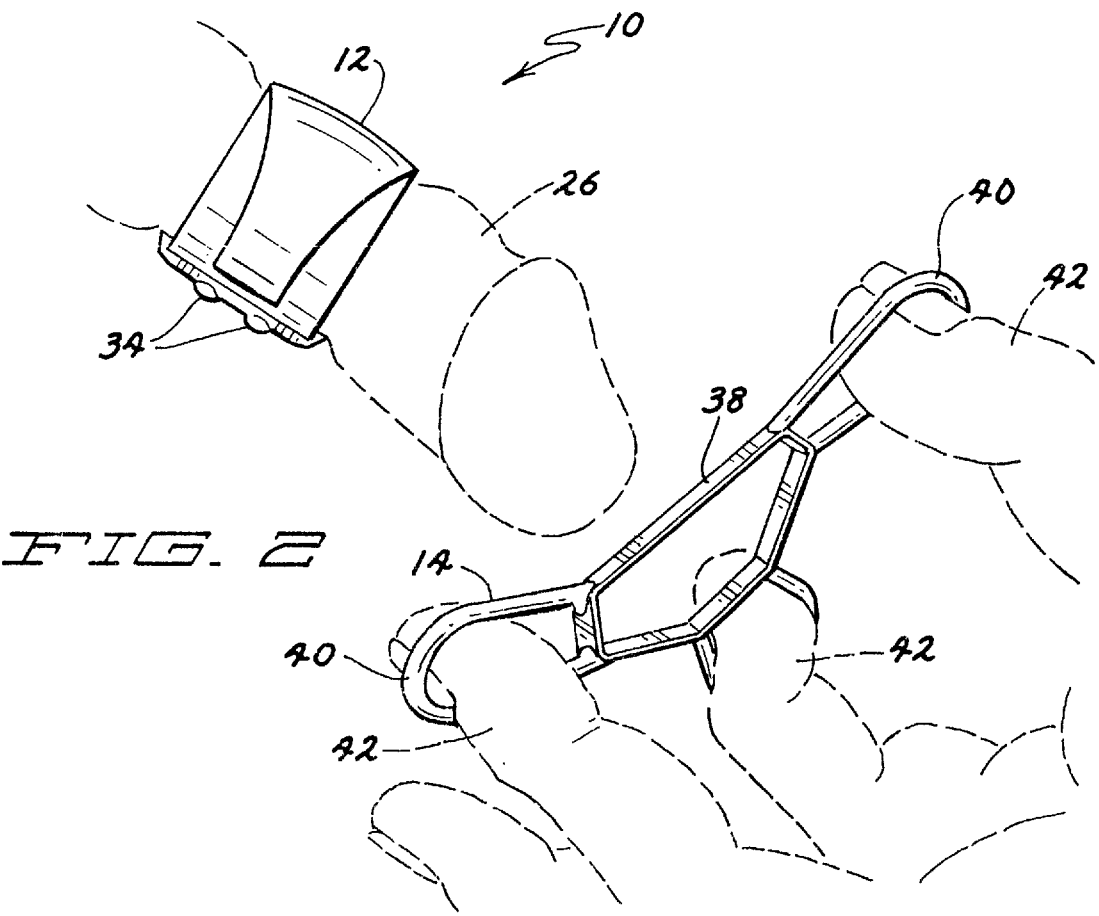
FIG. 2 is a perspective view of the urethral occlusion device of FIG. 1 with the occlusion band wrapped around the penis of the patient and the cincture band extended and being applied.
Figure 3:
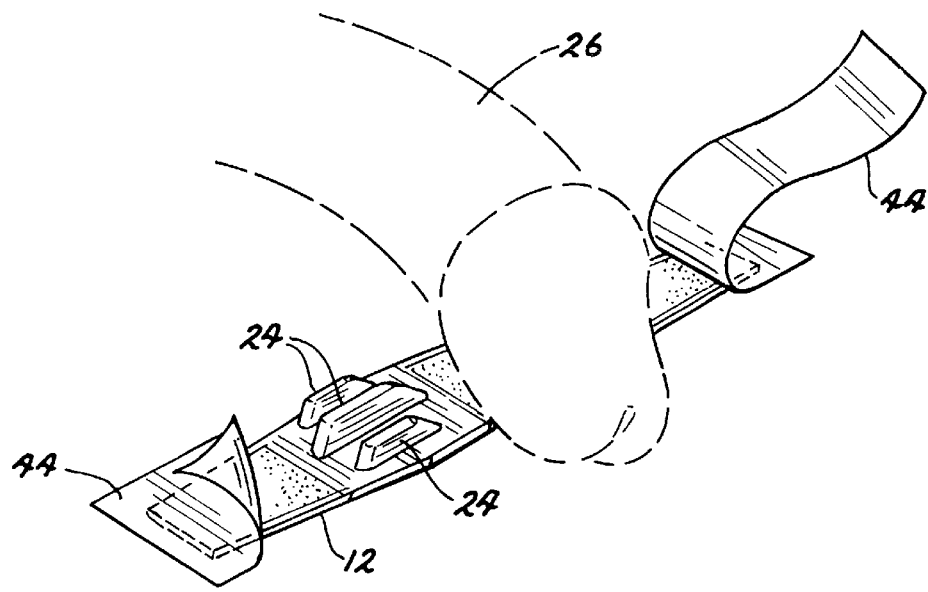
FIG. 3 is a perspective view of the occlusion band of the FIG. 1 in position to be wrapped surrounding the patient's penis.

Referring particularly to FIGS. 1 and 2, the urethral occlusion device 10 comprises two individual components referred to as an occlusion band 12 and a cincture band 14. The occlusion band 12 may be used separately, or with the cincture band 14. The embodiment of the cincture band 14 as described herein is not especially suited for separate use in treating urinary incontinence, but features of that cincture band 14 as described below may allow it to be utilized separately in other applications or with different types of urinary-related articles.

Figure 4:
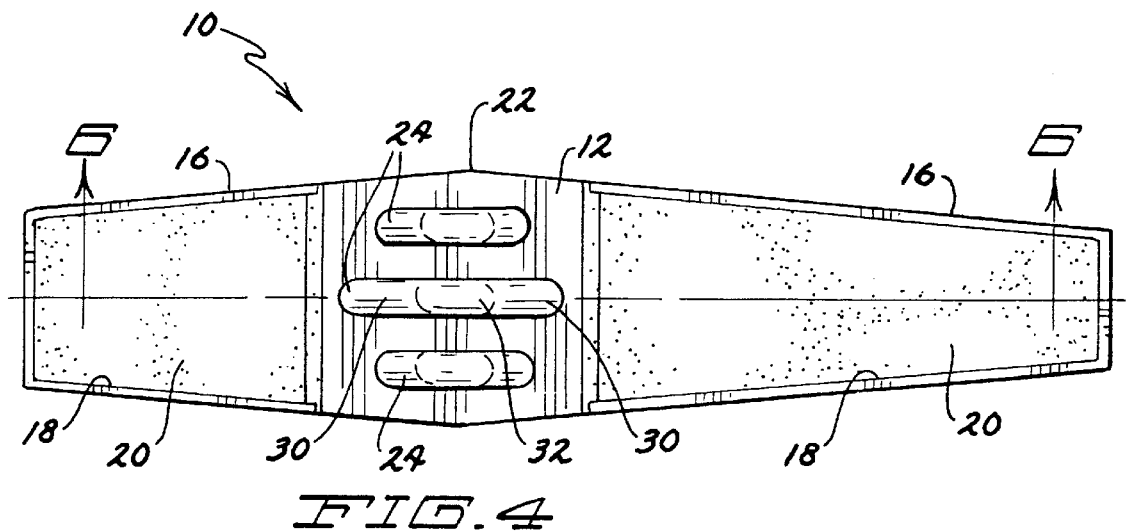
FIG. 4 is a top plan view of the occlusion band of FIG. 1.
Figure 5:
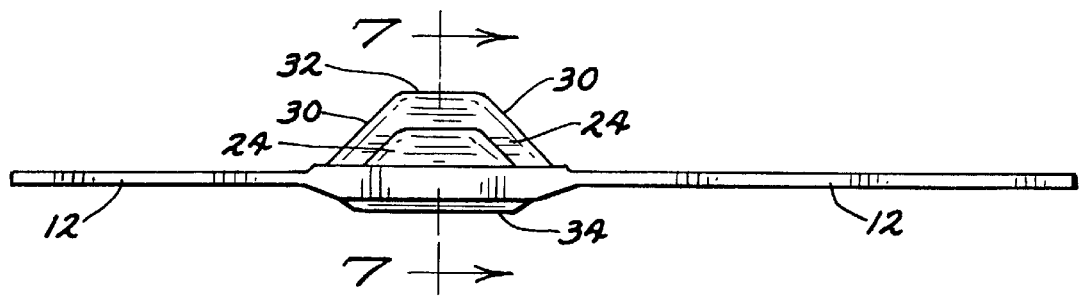
FIG. 5 is a side elevation view of the occlusion band of FIG. 4.
Figure 6:
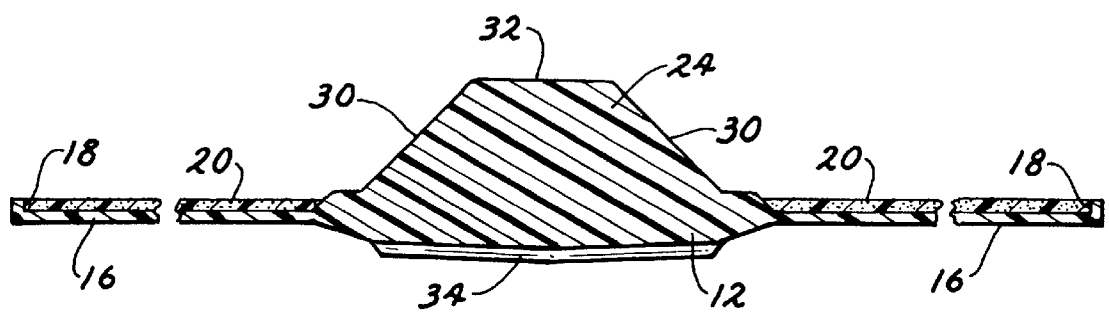
FIG. 6 is a side cross section view of the occlusion band of FIG. 4 taken through line 6—6 in FIG. 4.
Figure 7:
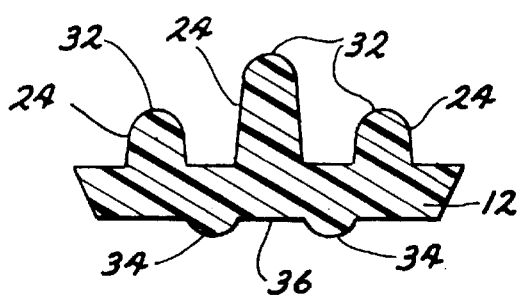
FIG. 7 is an end cross section view of the occlusion band of FIG. 4 taken through line 7—7 in FIG. 5.

The occlusion band 12 is fabricated from a shell 16 defining two opposing recessed areas 18, and a gel liner material 20 which fills those recessed areas to form two opposing gel inlays within the shell 16 which are exposed on the upper or top side of the occlusion band 12, as shown particularly in FIGS. 4 and 6. Together, the shell 16 and gel liner material 20 define the overall shape and consistency of the occlusion band 12.

The shell 16 is preferably fabricated from a cured liquid silicone rubber material such as dimethylsilicone which is sufficiently rigid to support and retain the gel liner material 20, but is highly flexible, compressible, and deformable, having a durometer rating of approximately 20A (Shore units) or less, particularly in the bulky or central body portions of the shell 16, and a tensile strength of 450 psi minimum, elongation of 650% minimum, and tear strength of 70 ppi minimum. One suitable example of such a material is LSR-10 liquid silicone rubber available under Product Identification No. 40023 from Applied Silicone Corporation of Ventura, Calif.

The gel liner material 20 is preferably a high strength firm silicone gel composition which is inherently tacky—exhibiting a peel strength of approximately 0.5 ppi (lb./in.) or less from a stainless steel surface—and hydrophobic so that it may be cleaned in water and reused without reduction in its intrinsic tackiness for silicone rubber or skin. One suitable example of such a silicone gel material is similarly available under Product Identification No. 40022 from Applied Silicone Corporation of Ventura, Calif. The materials utilized to fabricate the shell 16 and gel liner material 20, as well as their properties, characteristics, uses, and advantages, are additionally described in detail in U.S. patent application Ser. No. 08/760,906, the entire disclosure of which is incorporated herein by reference as though fully set forth. Both the shell 16 and gel liner material 20 preferably have a translucent, very slight white color closely bordering on transparent or clear, with the shell 16 and gel liner material 20 appearing substantially indistinguishable to the ordinary view of the patient. * * *

Referring again to FIGS. 1–7, the occlusion band 12 defines a generally planar, thin, flat band having a dual-tapered perimeter. The perimeter conforms to two truncated triangles joined at a common juncture or midpoint 22 and extending outwardly therefrom in opposing directions, one of the ends (on the right in FIG. 4) having a length slightly greater than the other such that it tapers to a slightly narrower width. The central portion of the occlusion band 12 is substantially thicker (approximately 2.5 times) than the opposing end portions, and defines one or more ribs 24 which project upwardly from the occlusion band 12 and inwardly toward the penis 26 and urethra 28 of the patient when the occlusion band 12 is wrapped thereabout, and which are oriented generally parallel with the longitudinal or lengthwise axis of the occlusion band 12.

In fabricating the occlusion band 12, the shell 16 including the ribs 24 is molded, and the gel liner material 20 is then poured into the recesses 18 defined by the shell 16 in a highly viscous liquid or syrup-like state and allowed to cure or dry. This process can occur at ambient temperatures or may be assisted by the suitable application of heat. Once cured or dried, the gel liner material 20 bonds securely with the compatable shell 16 material, and the exposed surface remains highly tacky both to skin and the opposing surface of the shell 16. However, if the tacky surface of the gel liner material 20 remains in contact with the opposing surface of the shell 16 for an extended period of time, the gel liner material 20 will not permanently bond with the shell 16 material because the gel liner material 20 has already cured or dried. Consequently, the gel liner material 20 will releasably adhere to the overlapped regions of the shell 16 which the gel liner material 20 contacts sufficiently for anchoring the occlusion band 12 when it is wrapped, but the exposed tacky gel liner material 20 which contacts the shell 16 will not be left behind on the shell 16 when the two components are peeled apart.

In this manner, the shell 16 acts both as a cohesive carrier of the gel liner material 20 which has an exposed tacky surface on the "front" side, and an attachable but releasable anchoring substrate for that exposed tacky surface of the gel liner material 20 on the opposing or "reverse" side. Due to the low shear or peel force properties of the gel liner material 20 when in contact with the "reverse" side of the shell 16, this structure also exhibits a self-limiting characteristic in that the occlusion band 12 cannot be wrapped too tightly or it will naturally unpeel or unwrap itself, thereby preventing inadvertent strangulation of constriction of blood circulation. When properly wrapped using the correct tension, the occlusion band 12 is prevented from inadvertently unpeeling or unwrapping, but will still provide occlusion. Consequently, when constructed according to this disclosure and properly sized for the particular patient (meaning selection of the appropriate rib 24 size and configuration as described below), the occlusion band 12 will stretch and occlude the patient's urethra 28 without exerting unnecessary compressive force on the penis 26, causing discomfort when worn, damaging the patient's skin when removed, or compromising the proper function of the patient's circulatory or urinary systems during long-term use.

In the embodiment shown in FIGS. 1–7, there are three ribs 24 spaced generally uniformly transversely across the occlusion band 12 each having a generally similar shape, the central rib 24 of which is higher and longer than the two ribs 24 disposed on the outer or opposing sides of the central rib 24. Each rib 24 is highly pliant, deformable, and compressible under gentle finger pressure, and defines a pair of angled or beveled side surfaces 30 which transition gradually into a radiused, truncated plateau or top surface 32.

A pair of spaced-apart, semi-circular beads 34 project a slight distance outwardly from the bottom or outer surface of the occlusion band 12, and are similarly oriented generally parallel with the longitudinal or lengthwise axis of the occlusion band 12. The beads 34 are spaced a distance sufficiently for the cincture band 14 to seat and obtain purchase on the flat region 36 therebetween, as described in further detail below.

Figure 11A:
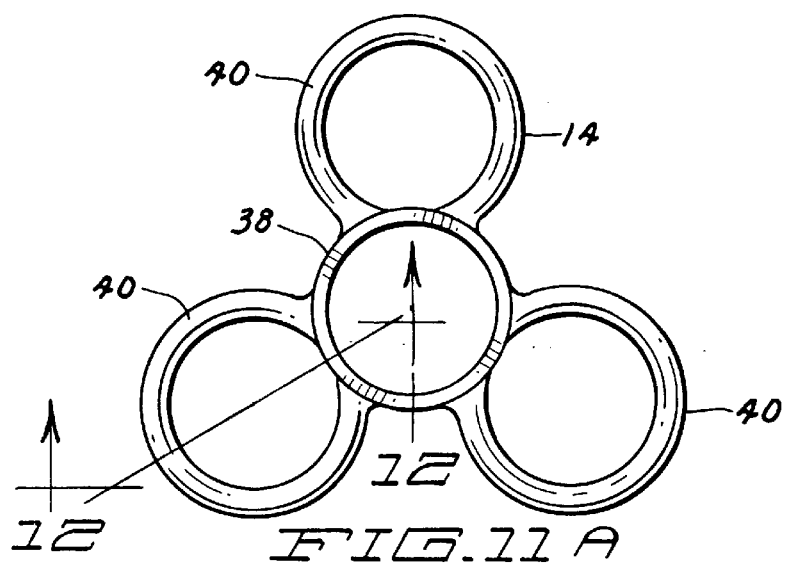
FIG. 11a is a plan view of the cincture band in the unstretched configuration.
Figure 11B:
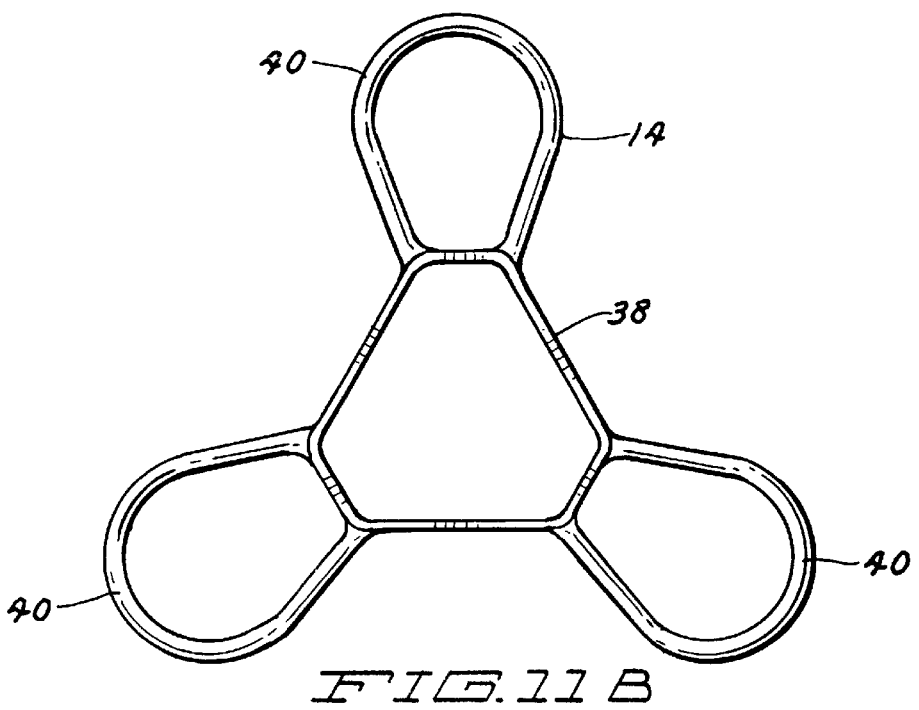
FIG. 11b is a plan view of the cincture band in the stretched configuration.

Referring particularly to FIGS. 1, 2, 11a, 11b, and 12, one embodiment of the cincture band 14 is shown in the unstretched and stretched configurations. The cincture band 14 is composed of a central pressure-exerting ring 38 integrally formed with or connected to three finger-engaging rings 40 positioned equidistantly around the periphery or circumference of the pressure-exerting ring 38. Each of the finger-engaging rings 40 has a thickness or cross-sectional area which is greater than that of the pressure-exerting ring 38 such that when the fingers 42 of the patient or a medical practitioner are inserted into the finger-engaging rings 40 as shown in FIG. 2 and pressure is exerted radially outward along three generally equidirected vectors, the pressure-exerting ring 38 will deform and stretch significantly more than the finger-engaging rings 40 will deform and stretch, thereby forming a central opening having a generally non-uniform hexagonal stretched shape as shown in FIGS. 2 and 11b and a larger circumference than would be achieved if the thickness or cross-sectional area of the pressure-exerting ring 38 and finger-engaging rings 40 were equivalent.

The cincture band 14 is preferably fabricated from a cured liquid silicone rubber material such as LSR-33 liquid silicone rubber having a durometer rating of approximately 33A (Shore units), and a tensile strength of 870 psi minimum, elongation of 650% minimum, and tear strength of 57 ppi minimum (one example being Baysilone LSR 4030).

Figure 8:
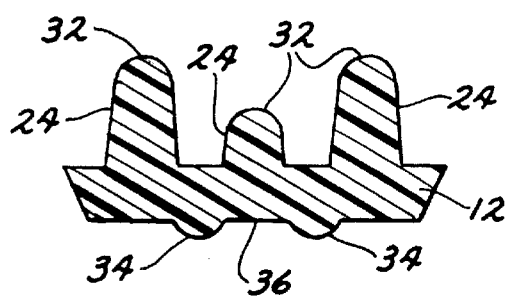
FIG. 8 is an end cross section view of an alternate embodiment of the occlusion band of FIG. 4 taken from the same vantage as FIG. 7.
Figure 10:
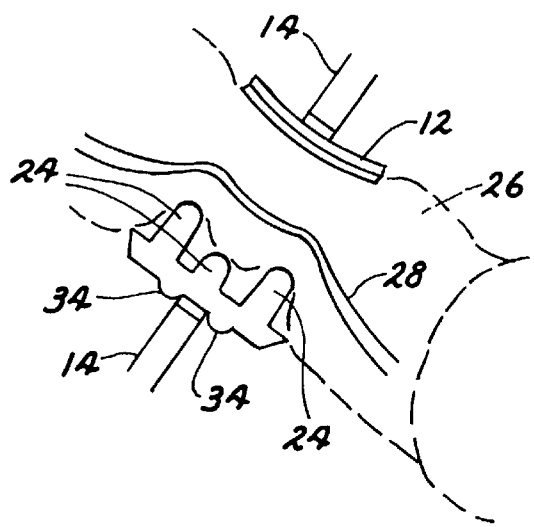
FIG. 10 is a is a side diagrammatic view of the occlusion band and cincture band of FIGS. 1 and 8 in place surrounding the patient's penis and occluding the urethra.

Referring to FIGS. 8 and 10, one alternate embodiment of the urethral occlusion device 10, the respective heights and orientation of the ribs 24 is reversed, to provide two taller ribs 24 disposed on opposing sides of a shorter central rib 24.

Referring particularly to FIGS. 1–3, 9, and 10, the method of using the urethral occlusion device 10 is shown. The patient peels the protective backing strips 44 which cover the tacky upper surface of the two regions of the gel liner material 20, and positions the occlusion band 12 beneath the penis 26 with the ribs 24 disposed generally beneath the urethra 28 and radially aligned therewith. The shorter end of the occlusion band 12 is wrapped upwardly around the side and across the top surface of the penis 26, and gently adheres in place to the skin of the patient. The opposing or longer end of the occlusion band 12 is similarly wrapped upwardly around the side and across the top surface of the penis 26 overlapping a portion of the shorter end of the occlusion band 12, and similarly adheres gently in place to the skin of the patient and to the outer surface of the shell 16 defining the shorter end of the occlusion band 12. The patient wraps the occlusion band 12 to the personally selected and desired degree of tightness which accomplishes the compression necessary to achieve sufficient occlusion of the urethra 28 and urinary retention for that patient during normal cycles of wearing the urethral occlusion device 10, but which remains comfortable and produces the least noticeable affects for the patient. As noted above, the self-limiting adhesive characteristics of the gel liner material 20 and shell 16 prevent the patient from applying too great a tension or compressive pressure when wrapping the occlusion band 12.

The patient then grips the cincture band 14 and inserts a thumb and fingers 42 into the finger-engaging rings 40, and applies force equidirectionally outward to stretch the pressure-exerting ring 38 to its stretched configuration, at which it is sufficiently expanded or enlarged so as to be easily placed over the circumference of the patient's penis 26 and the occlusion band 12 wrapped thereabout. The cincture band 14 is aligned with the transverse centerline of the occlusion band 12 and the stretching force is released so that the pressure-exerting ring 38 retracts to its unstretched position and rests in engaging contact parallel with and between the beads 34 defined by the outer surface of the occlusion band 12. The cincture band 14 thus exerts additional compressive pressure on the occlusion band 12 in the region of the ribs 24, and further holds or secured the occlusion band 12 in its wrapped configuration to prevent inadvertent unwrapping or unpeeling in the event the free end of the occlusion band 12 is pulled or caught, such as on the fabric of the patient's clothing.

Figure 9:
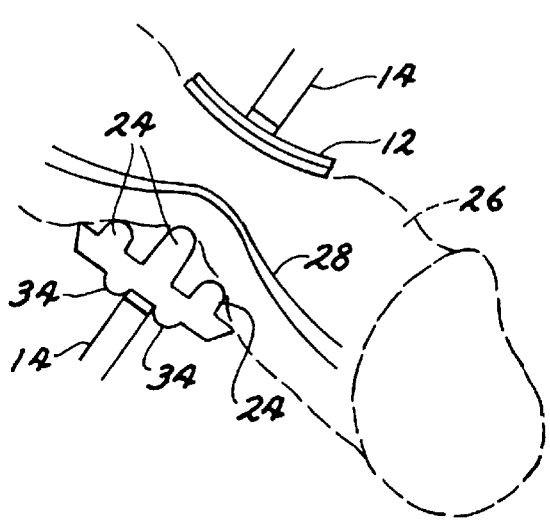
FIG. 9 is a side diagrammatic view of the occlusion band and cincture band of FIGS. 1 and 7 in place surrounding the patient's penis and occluding the urethra.

Referring to FIGS. 9 and 10, when the occlusion band 12 is properly applied to the penis 26 of the patient, the ribs 24 deform the underside of the penis 26 inwardly to gently stretch the urethra 28 and cause it to occlude, whereas the width of the occlusion band 12, the doubled layer of shell 16 material, and the great elasticity or deformability of the silicone rubber material prevent the occlusion band 12 from restricting blood circulation within or causing strangulation of the penis 26. It may be readily appreciated that selection of dimensions and properties for the cincture band 14 will similarly be dictated by the size and properties of the occlusion band 12 being used, and may be refined by experimentation and patient feedback.

For voiding or when not needed, the process is reversed to remove the cincture band 14 and the occlusion band 12, each of which may be washed using water and a mild non-solvent detergent (including a common household or bactericidal soap) and reused repeatedly. Given the relatively low cost and ease of manufacturing and packaging the urethral occlusion device 10, it may also be appreciated that the urethral occlusion device 10 renders itself suitable for use as a disposable item, on the order of one day's use per occlusion band 12, and longer term use of each cincture band 14. In the event that the patient's skin becomes irritated by or sensitive to prolonged contact with the gel liner material 20 or its periodic removal from the surface of the skin, the position of the occlusion band 12 on the penis 28 may be adjusted to permit previously covered portions to normalize.

Representative dimensions for the embodiments of the occlusion band 12 described herein include an overall length of approximately 5", a maximum width of approximately 1.2", and ends which taper to widths of 0.77" and 0.6" respectively. The thickness of the shell 16 is approximately 0.02" in the wall areas defining the recesses 18, and its overall height is 0.06" along the ends and 0.15" in the central portion. A "taller" version has ribs 24 which are approximate 0.33" and 0.165" in height, respectively, the center rib 24 of which has a 5° transverse taper and length of approximately 1.03" and a top surface of 0.3" between radiuses, the outer ribs 24 having lengths of approximately 0.7" and a spacing of 0.64" on center. A "shorter" version has ribs 24 which are approximate 0.23" and 0.12" in height, respectively, and lengths and widths substantially similar to the "taller" version. Each of the ribs 24 has a 0.08" radius at the top. The beads 34 are spaced approximately 0.33" apart, and each have a radius substantially the same as the ribs 24.

Figure 12:
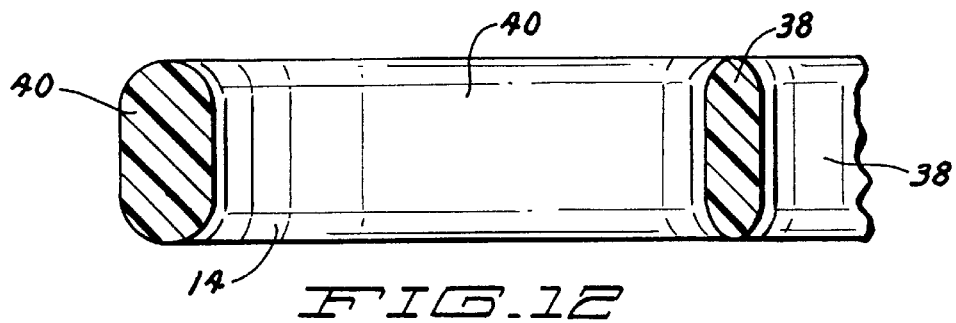

Representative dimensions for the embodiments of the cincture band 14 described herein include a pressure-exerting ring 38 having a diameter ranging between approximately 0.77" and 1.1", and finger-engaging rings 40 having diameters such that the distance between the radial centerpoints of the pressure-exerting ring 38 and each finger-engaging ring 40 ranges between approximately 0.77" and 0.94". Thus, the maximum overall width of he cincture band 14 varies between approximately 2.29" and 2.58". The height of the cincture band 14 may similarly vary from approximately 0.13" to 0.17", with a thickness of the pressure-exerting ring 38 remaining generally uniform at 0.07" with a 0.035" radius, and the thickness of the finger-engaging rings 40 remaining generally uniform at 0.125" with a 0.063" radius (in discrete regions of the pressure-exerting ring 38 and finger-engaging rings 40 as shown in FIG. 12, rather than junctions between the pressure-exerting ring 38 and finger-engaging rings 40 which have substantially greater and non-uniform thicknesses as those components transition into one another).

While the preferred embodiments of the above urethral occlusion device 10 have been described in detail with reference to the attached drawings Figures, it is understood that various changes, modifications, and adaptations may be made in the urethral occlusion device 10 and its method of use and fabrication without departing from the spirit and scope of the appended claims.

What is claimed is:

1. A urethral occlusion device for retaining urine in the bladder of a male patient having a penis and a urethra by occluding said urethra, said penis also having blood circulating through a vascular system therein, said apparatus comprising:

an occlusion band which is wrapped circumferentially about the penis and is fabricated from a flexible, deformable, elastomeric material, said occlusion band having an inner surface and an outer surface when wrapped about the penis, said occlusion band defining at least one region having an intrinsically tacky surface to contact and adhere to the penis and to said outer surface of said occlusion band, said occlusion band further defining at least one rib member extending from said inner surface of said occlusion band generally inward toward the urethra, said at least one rib member being generally pliant and deformable, said occlusion band applying sufficient pressure on said at least one rib member so as to press said at least one rib member inwardly into the penis so as to alter the path of the urethra and cause the urethra to stretch and become occluded to obstruct the flow of urine from the bladder, while simultaneously the occlusion band does not significantly interfere with the flow of blood circulating through the vascular system of the penis of the patient.

2. The urethral occlusion device of claim 1 wherein the occlusion band includes a shell member which defines a recess corresponding to the at least one region having an intrinsically tacky surface, and wherein the intrinsically tacky surface comprises:

a gel liner material disposed within the recess.

3. The urethral occlusion device of claim 2 wherein the shell member is fabricated from a cured liquid silicone rubber.

4. The urethral occlusion device of claim 3 wherein the shell member has a maximum durometer rating of approximately 20A (Shore units) or less.

5. The urethral occlusion device of claim 2 wherein the gel liner material is a high strength firm silicone gel composition.

6. The urethral occlusion device of claim 2 wherein the shell member and the gel liner material are hydrophobic and may be washed with water and a detergent for reuse.

7. The urethral occlusion device of claim 1 wherein the occlusion band has a shell member which defines the at least one rib member, said shell member having a maximum durometer rating of approximately 20A (Shore units) or less for the at least one rib member.

8. The urethral occlusion device of claim 1 wherein the occlusion band defines two opposing ends, each of said two opposing ends defining an opposing one of the at least one region having an intrinsically tacky surface.

9. The urethral occlusion device of claim 1 wherein the at least one rib member comprises a plurality of rib members.

10. The urethral occlusion device of claim 9 wherein the occlusion band has a longitudinal axis and each of the plurality of rib members has a direction of extent oriented generally parallel with said longitudinal axis of the occlusion band, such that the plurality of rib members are oriented generally parallel with one another and generally perpendicular to the urethra.

11. The urethral occlusion device of claim 9 wherein the number of the plurality of rib members is at least three.

12. The urethral occlusion device of claim 11 wherein the plurality of rib members includes a central rib member disposed between two opposing rib members, said central rib member having a height generally greater than that of said two opposing rib members.

13. The urethral occlusion device of claim 11 wherein the plurality of rib members includes a central rib member disposed between two opposing rib members, said central rib member having a height generally less than that of said two opposing rib members.

14. The urethral occlusion device of claim 9 wherein each of the plurality of rib members defines a generally truncated triangular shape with a generally longitudinally flat top surface.

15. The urethral occlusion device of claim 14 wherein the generally longitudinally flat top surface defines a transverse radius.

16. The urethral occlusion device of claim 1 wherein the at least one rib member defines a generally truncated triangular shape with a generally longitudinally flat top surface.

17. The urethral occlusion device of claim 16 wherein the generally longitudinally flat top surface defines a transverse radius.

18. The urethral occlusion device of claim 1 wherein the at least one region having the intrinsically tacky surface is initially covered by a protective backing material which is removed prior to the occlusion band being applied to the penis.

19. The urethral occlusion device of claim 1 wherein the at least one rib member extends to a height within the range of approximately 0.23" to approximately 0.33" relative to the inner surface of the occlusion band.

20. The urethral occlusion device of claim 1 further comprising:

a cincture band which circumscribes the occlusion band when the occlusion band is wrapped surrounding the penis of the patient, said cincture band applying additional compressive pressure to the at least one rib member to assist in achieving occlusion of the urethra of the patient.

21. The urethral occlusion device of claim 20 wherein the patient has a hand including a plurality of fingers, and wherein the cincture band comprises:

a pressure-exerting ring; and a plurality of finger-engaging rings connected to and extending from said pressure-exerting ring, said pressure-exerting ring having a cross-sectional area generally less that that of said plurality of finger-engaging rings such that when the patient inserts the plurality of fingers into said plurality of finger-engaging rings and exerts a radially outwardly-directed force thereon, said pressure-exerting ring will deform and stretch more than said plurality of finger-engaging rings deform and stretch.

22. The urethral occlusion device of claim 21 wherein the pressure-exerting ring and the plurality of finger-engaging rings are formed integrally with one another.

23. The urethral occlusion device of claim 21 wherein the pressure-exerting ring and the plurality of finger-engaging rings are fabricated from a cured liquid silicone rubber.

24. The urethral occlusion device of claim 21 wherein the pressure-exerting ring and the plurality of finger-engaging rings each have a generally oval shape, each of the plurality of finger-engaging rings having a cross-sectional thickness of approximately 1.8 times that of the pressure-exerting ring.

25. The urethral occlusion device of claim 21 wherein the pressure-exerting ring and the plurality of finger-engaging rings each have a generally oval shape, each of the plurality of finger-engaging rings having a cross-sectional thickness of approximately 0.125" and the pressure-exerting ring having a cross-sectional thickness of approximately 0.7".

26. The urethral occlusion device of claim 20 wherein the occlusion band defines a pair of beads projecting outwardly from the outer surface of the occlusion band, the cincture band seating between said pair of beads.

27. The urethral occlusion device of claim 26 wherein the occlusion band has a longitudinal axis and each of the pair of beads has a direction of extent generally parallel with said longitudinal axis of the occlusion band, each of said pair of beads being disposed generally proximate to and opposing the at least one rib member.

28. The urethral occlusion device of claim 20 wherein the cincture band comprises:
   a pressure-exerting ring defining a periphery; and
   three finger-engaging rings connected to and extending from said periphery of said pressure-exerting ring, said three finger-engaging rings being each positioned substantially equidistantly from one another around said periphery of said pressure-exerting ring.

29. A cincture band for use in providing compressive pressure around the penis of a patient, the patient having a hand including a plurality of fingers, said cincture band comprising:
   a pressure-exerting ring; and
   a plurality of finger-engaging rings connected to and extending from said pressure-exerting ring, said pressure-exerting ring having a cross-sectional area generally less that that of said plurality of finger-engaging rings such that when the patient inserts the plurality of fingers into said plurality of finger-engaging rings and exerts a radially outwardly-directed force thereon, said pressure-exerting ring will deform and stretch more than said plurality of finger-engaging rings deform and stretch.

30. The cincture band of claim 29 wherein the number of the plurality of finger-engaging rings is three, said plurality of finger-engaging rings being spaced equidistantly from one another around the pressure-exerting ring.

31. The cincture band of claim 29 wherein the pressure-exerting ring and the plurality of finger-engaging rings are formed integrally with one another.

32. The cincture band of claim 29 wherein the pressure-exerting ring and the plurality of finger-engaging rings are fabricated from a cured liquid silicone rubber material.

33. The urethral occlusion device of claim 29 wherein the pressure-exerting ring and the plurality of finger-engaging rings each have a generally oval shape, each of the plurality of finger-engaging rings having a cross-sectional thickness of approximately 1.8 times that of the pressure-exerting ring.

34. The urethral occlusion device of claim 29 wherein the pressure-exerting ring and the plurality of finger-engaging rings each have a generally oval shape, each of the plurality of finger-engaging rings having a cross-sectional thickness of approximately 0.125" and the pressure-exerting ring having a cross-sectional thickness of approximately 0.7".

35. An apparatus for retaining urine in the bladder of a male patient having a penis and a urethra by occluding said urethra, said penis also having blood circulating through a vascular system therein, said apparatus comprising:
   an occlusion band which is wrapped circumferentially about the penis and is fabricated from a flexible, deformable, elastomeric material, said occlusion band having an inner surface and an outer surface when wrapped about the penis, said occlusion band defining at least one region having an intrinsically tacky surface to contact and adhere to the penis and to said outer surface of said occlusion band, said occlusion band further defining at least one rib member extending from said inner surface of said occlusion band generally inward toward the urethra, said at least one rib member being generally pliant and deformable, said occlusion band applying sufficient pressure on said at least one rib member so as to press said at least one rib member inwardly into the penis so as to alter the path of the urethra and cause the urethra to become occluded to obstruct the flow of urine from the bladder, while simultaneously the occlusion band does not significantly interfere with the flow of blood circulating through the vascular system of the penis of the patient.

36. The apparatus of claim 35 wherein the occlusion band defines at least one region having an intrinsically tacky surface to contact and adhere to the penis or to the outer surface of the occlusion band or both, the occlusion band further comprising:
   a shell member defining a recess therein, said recess generally conforming to the at least one region having an intrinsically tacky surface, said shell member being fabricated from a cured liquid silicone rubber material; and
   a gel liner material disposed within said recess of said shell member, said gel liner material being a high strength firm silicone gel composition.

37. The apparatus of claim 36 wherein the shell member forms a cohesive carrier for the gel liner material having an exposed tacky surface on a front side of the shell member, and an attachable but releasable anchoring surface on a reverse side of the shell member.

38. An occlusion band for retaining urine in the bladder of a male patient having a penis and a urethra by occluding said urethra, said penis also having blood circulating through a vascular system therein, said occlusion band comprising:
   a shell member fabricated from a generally elastomeric material; and
   a gel liner material bonded to said shell member, such that said shell member forms a cohesive carrier for said gel liner material having an exposed tacky surface on a front side of said shell member, and an attachable but releasable anchoring surface on a reverse side of said shell member, whereby said tacky surface is adapted to adhere to the penis and to said releasable anchoring surface, and
   whereby the occlusion band is wrapped circumscribing the penis of the patient to apply sufficient pressure so as to alter the path of the urethra and cause the urethra to become occluded to obstruct the flow of urine from the bladder, while simultaneously not significantly interfering with the flow of blood circulating through the vascular system of the penis of the patient.

39. The occlusion band of claim 38 further comprising:
   at least one rib member connected to and extending from the front side of the shell member inwardly toward the urethra, said at least one rib member being generally pliant and deformable, said occlusion band applying sufficient pressure on said at least one rib member so as to press said at least one rib member inwardly into the penis so as to alter the path of the urethra and cause the urethra to stretch and become occluded to obstruct the flow of urine from the bladder.

40. A method for retaining urine in the bladder of a male patient having a penis and a urethra by occluding said urethra, said penis also having blood circulating through a vascular system therein, said method comprising the steps of:

providing an occlusion band which is fabricated from a flexible, deformable, elastomeric material, said occlusion band having an inner surface and an outer surface, said occlusion band defining at least one region having an intrinsically tacky surface to contact and adhere to the penis and to said outer surface of said occlusion band, said occlusion band further defining at least one rib member extending from said inner surface of said occlusion band, said at least one rib member being generally pliant and deformable; and wrapping said occlusion band circumferentially about the penis such that said at least one rib member is oriented generally radially towards and is generally aligned with the urethra, and such that said at least one region having an intrinsically tacky surface contacts and adheres to either the penis or the outer surface of the occlusion band or both, said occlusion band being wrapped so as to apply sufficient pressure on said at least one rib member so as to press said at least one rib member inwardly into the penis so as to alter the path of the urethra and cause the urethra to stretch and become occluded to obstruct the flow of urine from the bladder, while simultaneously the occlusion band does not significantly interfere with the flow of blood circulating through the vascular system of the penis of the patient.

41. The method of claim 40 wherein the step of providing the occlusion band further includes providing an occlusion band having a shell defining a recess, and the at least one region having an intrinsically tacky surface is a gel liner material disposed within said recess.

42. The method of claim 41 wherein the step of providing the occlusion band further includes providing the shell fabricated from a cured liquid silicone rubber and the gel liner material from a high strength firm silicone gel composition.

43. The method of claim 40 wherein the step of providing the occlusion band further includes providing the occlusion band with a plurality of rib members of differing relative heights.

44. The method of claim 40 further comprising the steps of:

providing a cincture band; and applying said cincture band in circumscribing relation to the occlusion band when the occlusion band is wrapped surrounding the penis of the patient, said cincture band applying additional compressive pressure to the at least one rib member to assist in achieving occlusion of the urethra of the patient.

45. The method of claim 44 wherein the patient has a plurality of fingers and wherein the step of providing the cincture band further comprises the step of:

providing a cincture band having a pressure-exerting ring and a plurality of finger-engaging rings connected to and extending from said pressure-exerting ring, said pressure-exerting ring having a cross-sectional area generally less that that of said plurality of finger-engaging rings such that when the patient inserts the plurality of fingers into said plurality of finger-engaging rings and exerts a radially outwardly-directed force thereon, said pressure-exerting ring will deform and stretch more than said plurality of finger-engaging rings deform and stretch.

* * * * *